United States Patent [19]
Parham et al.

[11] Patent Number: 5,418,061
[45] Date of Patent: * May 23, 1995

[54] MICROPOROUS POLYSULFONE SUPPORTS SUITABLE FOR REMOVAL OF LOW DENSITY LIPOPROTEIN-CHOLESTEROL

[75] Inventors: Marc E. Parham, Bedford; Richard L. Duffy, Cambridge, both of Mass.

[73] Assignee: W. R. Grace & Co.-Conn., New York, N.Y.

[*] Notice: The portion of the term of this patent subsequent to Feb. 16, 2010 has been disclaimed.

[21] Appl. No.: 95,617

[22] Filed: Jul. 21, 1993

Related U.S. Application Data

[63] Continuation of Ser. No. 882,985, May 14, 1992, abandoned, which is a continuation-in-part of Ser. No. 618,791, Nov. 27, 1990, Pat. No. 5,187,010.

[51] Int. Cl.6 .................... B01D 63/02; B01D 69/08
[52] U.S. Cl. ..................................... 428/398; 428/364
[58] Field of Search ............... 428/398, 400, 364, 373, 428/378; 210/500.35, 500.41, 500.23; 521/27

[56] References Cited

U.S. PATENT DOCUMENTS

| | | | |
|---|---|---|---|
| 4,708,799 | 11/1987 | Gerlach | 428/398 |
| 4,874,522 | 10/1989 | Okamoto | 210/500.4 |
| 4,938,778 | 7/1990 | Ohyabu | 623/66 |
| 4,940,541 | 7/1990 | Aoyagi | 427/230 |
| 5,187,010 | 2/1993 | Parham et al. | 428/398 |

FOREIGN PATENT DOCUMENTS

| | | |
|---|---|---|
| 1163574 | 3/1984 | Canada . |
| 0087807 | 5/1985 | Japan . |
| 1212305 | 9/1986 | Japan . |
| 63-232845 | 9/1988 | Japan . |

OTHER PUBLICATIONS

Thies et al., Artificial Organs, 12, 320, 1988.
Naito, Artificial Organs, 13, 190, 1989.

*Primary Examiner*—Gollamudi S. Kishore
*Attorney, Agent, or Firm*—Bharat C. Gandhi

[57] ABSTRACT

The present invention relates to the efficient removal of low density lipoprotein cholesterol complex (LDL-C) from whole blood. More specifically, it relates to a microporous plasmapheresis support having an immobilized affinity agent. The immobilized affinity agent is polyacrylic acid bound directly and/or through an interaction with silica and/or calcium chloride to a microporous polysulfone support.

8 Claims, 1 Drawing Sheet

MICROPOROUS POLYSULFONE SUPPORTS SUITABLE FOR REMOVAL OF LOW DENSITY LIPOPROTEIN-CHOLESTEROL

This is a continuation of application Ser. No. 07/882,985 filed May 14, 1992, now abandoned, which is a continuation-in-part of U.S. Ser. No. 618,791, filed Nov. 27, 1990, now U.S. Pat. No. 5,187,010.

TECHNICAL FIELD

The present invention relates to the efficient removal of low density lipoprotein cholesterol complex (LDL-C) from whole blood. More specifically, it relates to the use of an immobilized affinity agent on a microporous plasmapheresis support. The immobilized affinity agent is polyacrylic acid bound directly and/or through an interaction with amorphous silica and/or a calcium ion containing compound to a microporous polysulfone membrane or support.

BACKGROUND

Atherosclerosis is the thickening and loss of elasticity in the inner walls of arteries, accompanied by the formation of small fatty modules on the artery walls and degeneration of the affected area. Atherosclerosis presented in the form of coronary heart disease and cerebrovascular diseases are major causes of morbidity and mortality in many industrial countries. Elevated plasma levels of low density lipoprotein-cholesterol complex (LDL-C) correlate with an increased risk for the development of atherosclerosis.

Patients at high risk for atherosclerosis are encouraged to make dietary changes in an attempt to control LDL-C levels. However, patient compliance is not always high and there is a large patient population which cannot control LDL-C levels merely through dietary modifications.

Drug therapy is also commonly used to try to lower LDL-C levels. While drug therapy is effective for many patients, there are still a large number of patients who are resistant to drug therapy or who suffer too many side effects to warrant its use.

In addition to dietary changes and drug therapy, attempts have been made to remove LDL-C directly from the plasma of patients through extracorporeal methods. These methods include plasma exchange, filtration based on molecular size, immunoadsorption, heparin precipitation and dextran sulfate adsorption. While these methods effectively remove LDL-C from plasma, they also remove varying quantities of desirable plasma components. The plasma exchange method removes all plasma and replaces the volume with plasma or albumin replacement solutions. All valuable plasma components, such as high density lipoprotein (HDL), and proteins such as albumin, IgG and clotting factors are removed in addition to the LDL-C. The other methods, while better than plasma exchange, have varying degrees of specificity for only LDL-C. With filtration based on molecular size, there is considerable loss of proteins with molecular weights greater than 250-400 kD. Immunoabsorption is specific for LDL-C only, but its efficiency for removal of LDL-C is not as great as other methods. Heparin precipitation and dextran sulfate adsorption remove LDL-C, but a loss of 20-40% of HDL is generally expected; also the adsorbing capacities are fairly low. Since HDL plays an important role in reducing a patient's risk for atherosclerosis, a method which eliminates or minimizes the loss of HDL is highly desirable.

Previous filtration methods have also utilized carriers, such as agarose beads, which lack mechanical strength, and as a result are difficult to handle and operate. When fluid is passed through these carriers, there is a high probability of blockage. Additionally, these carriers may be destroyed by sterilization techniques. These carriers might also leach materials into the patient fluid.

Polyacrylate has been tested as a sorbent for lipoproteins from human plasma (Thies et al., *Artificial Organs* (1988) 12(4):320-324). Negligible loss of HDL and plasma proteins was shown with this absorbent. Polyacrylate has been attached to cellulosic beads through amide linkages. While the preparation was useful, it was not optimal for the treatment of whole blood. As mentioned previously, cellulosic beads do not have good mechanical strength, block easily, and are not easily sterilized.

Kuroda et al. (EP 0143369) describe a porous adsorbent for absorbing low density lipoproteins having a silanol group and a synthetic polyanion linked with the surface. To prevent clogging, the porosity of the adsorbent must be distributed over a broad diameter range. By contrast, the microporous membrane of the present invention has uniform pore diameters. Murakami (Japanese P.A. 01-229878) describes porous polyester fibers coated with methacrylic acid which are useful to remove bilirubin or LDL from body fluids. Sterilization of polyester fibers can be problematic. Kuroda et al. (Japanese P.A. 63-232845) describe an absorbent material having on its surface a synthetic linear polymer which has both a carboxyl group and sulfate or sulfonate groups.

Polysulfone structures have not been used in the prior art with immobilized affinity due to the difficulties associated with the essentially non-reactive polysulfone surfaces. The coupling reactions taught in the prior art are not applicable to polysulfone surfaces. The ability to immobilize the affinity agent to a polysulfone surface by interpenetrating network has not previously been known.

SUMMARY OF THE INVENTION

This invention provides a support for binding low density lipoprotein cholesterol complex (LDL-C) from whole blood or plasma. The support is a microporous polysulfone structure which has immobilized affinity agent on the surface. The immobilized affinity agent is a polyanion, such as polyacrylic acid which is bound directly and/or through an interaction with silica and/or a calcium ion containing compound to the microporous polysulfone structure by an interpenetrating network.

DETAILED DESCRIPTION OF THE INVENTION

Figure 1:
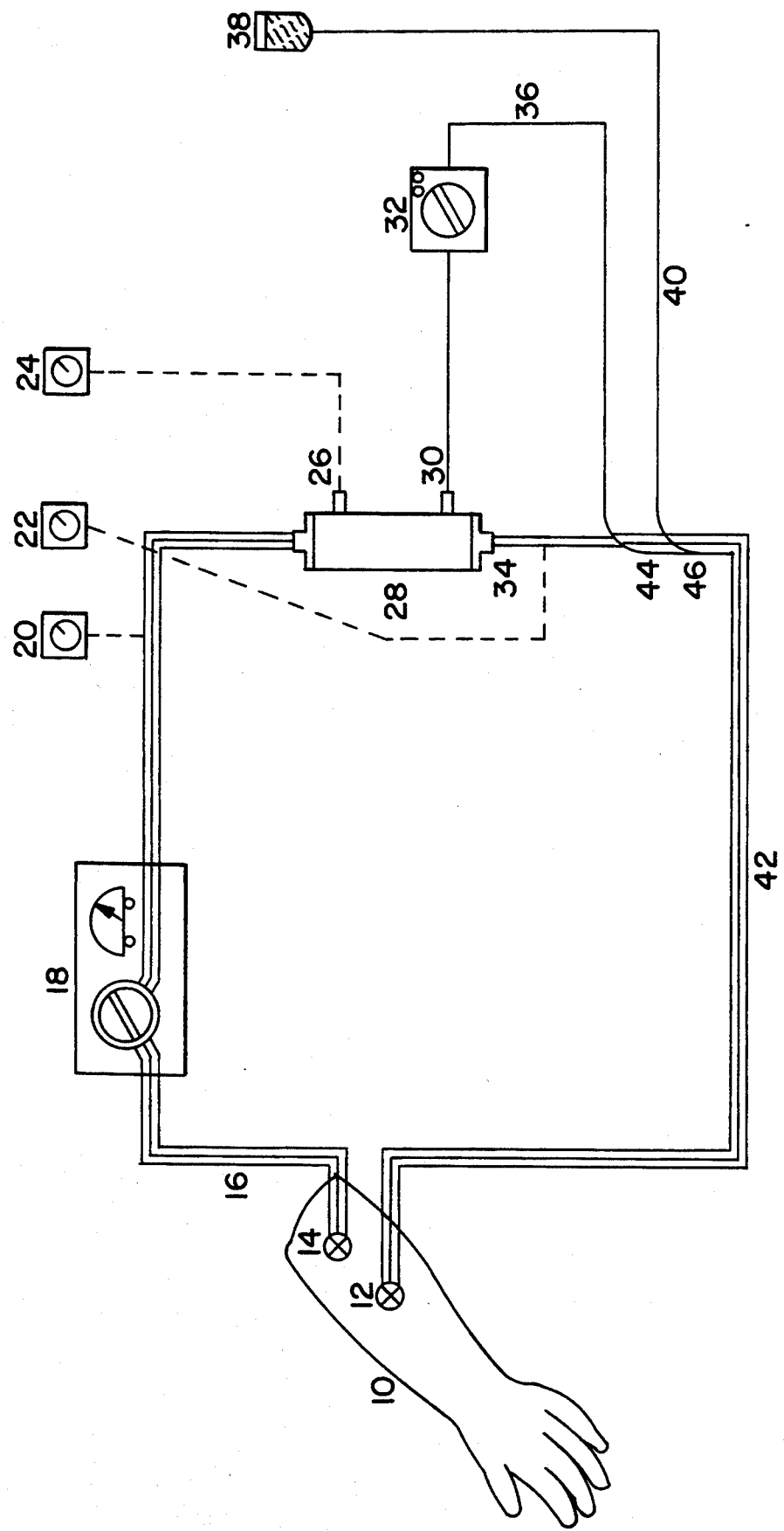
FIG. 1 is a schematic diagram indicating the action of one embodiment of the invention.

A support has been discovered which has properties that are advantageous for the removal of the complex of low density lipoprotein and cholesterol (LDL-C) from whole blood or plasma. The support is a microporous polysulfone structure which has polyacrylic acid immobilized on its surface. The support has desirable mechanical and specificity characteristics for its intended purpose of LDL-C removal. The support can also be sterilized by autoclaving techniques.

The Polysulfone Structure

The supports of this invention comprise porous polysulfone-based polymeric structures. Polysulfones are a known class of polymers which have been used to form various types of membranes. Polysulfone structures are of a substantially non-flexible physical form. The microporous polysulfone support can take any desirable shape or form, including but not limited to porous hollow fiber membranes, porous flat sheet membranes or microporous beads.

"Polysulfone", "polyarylsulfone", "polyether sulfone", and "polyarylether sulfone" are each intended to define a polymeric material having a combination of sulfone groups, aryl groups, and ether groups in the polymer chain and which may also contain alkylene groups therein. Polysulfone (PS) polymers are available in a variety of grades with respect to molecular weight, additives, etc. High molecular weight polysulfones may be preferred for preparation of membranes with additional strength. UDEL® P-1700, and UDEL® 3500 polysulfone polymers (Amoco Performance Products Inc.) are suitable. Other suitable commercially available polysulfones are under the tradenames of ASTREL® (3M), VICTREX® (ICI), and RADEL® (Amoco). Polysulfone is used as the primary polymeric component of the porous support because of such beneficial characteristics as thermal stability, resistance to acid, alkali and salt solutions, high mechanical strength, etc.

The polysulfones found useful as support components of the present invention are polyaryl ether sulfones. The polysulfone can be viewed as having recurring units which is shown below:

where the SO$_2$ group may be in the ortho, meta or para position on the ring and where R represents

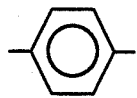

or

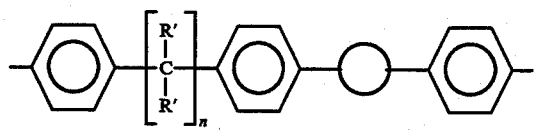

wherein n is an integer of 0 to 3 (preferably 0 or 1) and each R' independently is selected from hydrogen or a C$_1$–C$_3$ alkyl, preferably methyl. The above polyarylether sulfones may be used as homopolymers or as copolymers of the polymeric groups described above where R is selected from more than one of the groups described hereinabove. Further, the above polyarylether sulfones may be formed into copolymers with polysulfone groups which are void of ether groups therein such as:

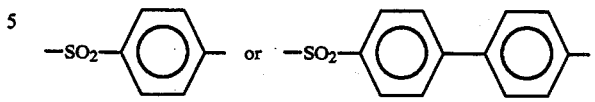

and the like. The homopolymers and copolymers described above can be used as the sole polymeric component or mixtures or blends of the homopolymers and/or copolymers can be used as the support component. The formation of blends provides polymeric component which can have customized properties. For example, it is known that increase in ether oxygen and/or alkylene groups in the subject polymers provides decrease in the soften temperature of the polymeric component and, therefore, aids in providing a composition which can be processed at a designed temperature. The subject polysulfones can be prepared by known manners.

The polysulfones used herein should have a weight average molecular weight of from about 20,000 to about 200,000, preferably at least about 50,000 to about 150,000. The polymer Tg will be dependent upon the structure of the polymer as described above and can be determined by one skilled in the art by conventional analytical means.

The subject polysulfones have benzylic hydrogens which can be independently substituted by non-dissociative groups, such as alkyl (preferably C$_1$–C$_3$ alkyl) or halogen (preferably chlorine) or by a dissociative group, such as sulfonic or carboxylic acid group. Each of the aryl groups may be unsubstituted or substituted with one or more of particular groups described above or may be substituted by different groups on a single aryl group or each on different aryl groups.

Other polymers or prepolymers can be used in combination with the polysulfone polymer, if desired, to impart various characteristics to the support. Polyethylene glycol (PEG), polyvinyl pyrrolidone (PVP) or any of a variety of polyurethane prepolymers may be used with the polysulfone to prepare these supports. Polymers or prepolymers are added to the polysulfone polymer in order to modify the structure and surface characteristics of the polysulfone structure. The additional polymer or prepolymer becomes an integral part of the polysulfone structure.

A. The Casting Solution

The casting solution is a multicomponent solution comprising polymeric and solvent components. The primary polymeric component will be the polysulfone polymer. The polymeric component would, of course, also comprise any other polymer or prepolymer which is used together with the PS polymer to form the membranes. Where reference is made to the polysulfone solution or casting solution, it is intended to include all polymeric components. That is, it will include the polysulfone polymer and, where appropriate, it also will include a selected additional polymer or prepolymer as described above.

The solvent component of the casting solution must be one in which polysulfone (as well as any other polymer or prepolymer used) is soluble. The polysulfone polymer is soluble in various solvents, such as 4-butyrolactone, N-methylpyrrolidone (N-MP), dimethylformamide (DMF), N,N-dimethylacetamide (DMA), cyclohexanone, and chloroform. 4-Butyrolactone is the preferred solvent.

At least about 8.0 wt. % and up to about 35.0 wt. % polysulfone in solvent should be used, preferably about 8.0 to about 22.0 wt. %. Above 35 wt. %, it will be difficult or impossible to dissolve the polysulfone in the solvent. Below about 8%, precipitation will be too slow for formation of hollow fibers, and the fibers are too fragile to handle practically. Up to about 20.0 wt. % of a second polymeric component, that is, one or more of the polymers or prepolymers described above, can be added to the PS solution.

The casting solution can also contain silica. Silica can be present in amounts of about 0.1 to about 10% wt/wt, preferably about 5%. The silica does not dissolve in the casting solution, but rather forms a slurry. The silica aids in the immobilization of polyacrylic acid to the membrane during the next step of processing. Silica acts as a pore former and viscosifier to achieve a microporous structure with a nominal pore size of about 0.4 micron to about 0.65 micron. The casting solution can also contain a polyanion such as polyacrylic acid (PAA). PAA can be present in amounts of about 0.01 to about 2% wt/wt, preferably about 0.5–1%.

B. Precipitation Solution

The precipitation or coagulation mechanism of microporous polysulfone structure formation is affected by the composition of the precipitation solution as well as that of the casting solution, and the composition of these two solutions are interdependent. In this disclosure, the terms "precipitation solution", "coagulation solution," "quench solution," and "quench bath" are used interchangeably to refer to the solution in which the porous polysulfone structure is formed. For formation of hollow fiber membranes, both an outer and a center precipitation or quench solution will be employed. The solvent content of the precipitation solution controls the rate at which the solvent comes out of the casting solution. In turn, this controls the rate of increase of the polymer concentration to the point at which the polymeric component precipitates out of the casting solution to form the porous polysulfone structure. The same solvent usually is used in the casting solution and the precipitation solution. 4-butyrolactone and blends of 4-butyrolactone and N-methyl-pyrrolidone are the preferred solvents. Other solvents are discussed above with regard to casting solutions.

A non-solvent is used in the precipitation solution in order to precipitate the polymer from the casting solution, thus causing formation of the porous polysulfone structure. For practical and economical purposes, it is preferred to use water as the non-solvent component of the precipitation solution. However, other non-solvents such as methanol, ethanol, propanol, butanol, ethylene glycol, acetone, methyl ethyl ketone, or the like, can be used instead of water, particularly when the solvent is water-immiscible. Alternatively, water and one or more other non-solvents can be used together.

In utilizing the method of this invention to prepare hollow fiber membranes, the precipitation solution used for the outer quench bath may be different from that used for the center quench fluid. In the preferred embodiment of this invention, the outer precipitation solution is water, and the center precipitation solution is 4-butyrolactone. Other solvents and non-solvents can be used as described above. In hollow fiber production, the center quench and outer quench are different phenomena. At center quench, a small volume of solution is used, which is almost in a static mode as compared with the casting solution. Conversely, the outer quench bath is present in large volumes and in a dynamic mode.

C. Polysulfone Structure Formation

The polysulfone structure of the present invention can take any suitable form that can provide for the removal of LDL-C from whole blood or plasma. The polysulfone structure should be microporous having pore sizes in the range of about 0.1 microns to about 0.7 microns, preferably between about 0.4 and 0.65 microns. A preferred structure is a hollow fiber membrane. Other suitable structures include, but are not limited to, flat sheet membranes, beads, or any other regularly or irregularly shaped particle-type support structure.

i. Hollow Fiber Spinning Conditions

In preparing the hollow fiber membranes of this invention, a liquid-liquid or wet spinning process is used similar to that described in U.S. Pat. No. 4,970,030. That is, the casting solution is fed through an extrusion die (spinnerette) directly into a precipitation bath, while simultaneously introducing the center quench fluid through the central aperture of the spinnerette to mechanically maintain the hollow center hole of the fiber. The fiber is fabricated and simultaneously quenched as it is drawn through the precipitation bath. By using this wet-spinning process, fibers with homogeneous pore structure and membrane morphology are produced.

One of the key factors in preparation of the hollow fiber membranes of this invention is use of the wet spinning process; that is, spinning the casting solution under water. In addition, selection of appropriate solutions for the inner and outer precipitation baths is important, as is the appropriate drawing or spinning rate of the fiber as it is formed. The presence of the center quench fluid also allows for simultaneous polymer precipitation from both the inner and outer surfaces of the fiber. The spinning rate is adjusted to allow for exchange of components between the casting and precipitation solutions. The solvent is leached out of the casting solution and is replaced by the non-solvent from the precipitation solution. As a consequence, polymer precipitation occurs, leading to formation of the membrane.

Too rapid a drawing rate will cause breakage due to insufficient membrane formation to maintain membrane integrity or will cause elongation or deformation of the pores. Conversely, too slow a drawing rate will cause defects resulting from excessive pressure by the center quench solution, which may cause blow-outs in the fiber structure; also, non-circular fibers are produced. The preferred drawing rate will depend in part on the casting solution viscosity and temperature and in part on the factors described below. However, the drawing rate typically will be in the range of about 3.0 to about 30.0 feet per minute, preferably about 7.0 to about 15.0 feet per minute, and will produce round fibers.

The precise spinning conditions are adjusted in order to yield hollow fibers meeting the desired physical requirements of inner diameter and wall thickness. centering of the central aperture of the spinnette is required in order to achieve a fiber having a uniform wall thickness. Any spinnerette suitable for the preparation of hollow fiber membranes may be used to prepare the membranes of this invention, however, quartz or glass spinnerettes are preferred in order to achieve the small inside diameters required of the hollow fibers of the invention. The spinning conditions left to be adjusted are the flow rate and pressure of the casting solution and the flow rate and pressure of the center quench fluid. These adjustments are well within the knowledge and ability of one of ordinary skill in this art. The preferred temperature for the casting solution will be in the range of ambient temperatures, although higher temperatures, e.g., up to about 70° C., may be employed to reduce the viscosity of the casting solution.

The dimensional and porosity characteristics of the membranes of this invention are such that LDL-C can pass through the fiber wall but most blood cells do not. Hemolysis occurs if numerous blood cells pass through the fibers, which is highly undesirable. However, passage of a small number of red blood cells through the fiber is acceptable. Generally speaking, membranes can be prepared which possess a pore diameter of between about 0.1 microns to about 0.7 microns, preferably between 0.4 and 0.65 microns. The inner diameter of the hollow fibers can range from about 150 to about 400 microns, preferably about 325 microns. The wall thickness can range from about ten to several hundred microns, preferably about 75 to about 100 microns.

ii. Flat Sheet Membrane Formation

Flat sheet membranes can be fabricated by casting the casting solution directly onto a rigid nonporous surface such as glass, stainless steel, or the like. Since the membrane is supported during precipitation, precipitation can be at a slower rate than the hollow fiber membranes described above. This affords greater flexibility in preparing the casting and precipitation solutions. However, the guidelines given above will apply generally to flat sheet membrane formation as well.

Membrane casting may be with a casting knife, and membranes may be cast onto the support at the desired thickness (i.e., 2.0 to 15.0 mils, preferably 4.0 to 10.0 mils). The membrane is cast onto the support directly in the precipitation bath, without exposure to air. When membrane formation is complete, the membrane separates from the nonporous support.

iii. Bead Formation

Beads can be fabricated by forcing the casting solution through a capillary and dropping the casting solution directly into a precipitation bath comprising a nonsolvent such as water. The resultant beads of variable sizes, as determined by drop height and orifice of extrusion capillary dimensions, are collected by vacuum filtration.

D. Silica Removal

Polysulfone structures which have been prepared from a casting solution containing silica are optionally treated to .remove residual silica. Silica which is not an integral part of the polysulfone structure network and is exposed to the bulk solution can be removed by treating the structure in a strong basic solution. The basic solution can be any basic conditions, preferably 0.3N to 2.5N sodium hydroxide, most preferably 1.0N to about 2.0N sodium hydroxide. The structure is generally treated with the basic solution for greater than 5 hours at room temperature. Structures with silica are not microporous until the structures are treated in the base to remove the bulk of the silica. The basic solution also aids in endotoxin removal. After this basic treatment, the structure can optionally be treated with an acidic solution (i.e., approximately 0.1N HCl) to further aid in endotoxin removal prior to polyacrylic acid immobilization.

E. Polyacrylic Acid Immobilization

Polyacrylic acid (PAA) is a selective affinity agent for LDL-C. Other suitable polyanions, such as methylmethacrylate can be substituted for polyacrylic acid. The presence of PAA on the surface of the porous PS structure enables the effective removal of LDL-C from the plasma components of whole blood. Polyacrylic acid is immobilized on the surface of the structure walls when the fibers are heated under pressure, preferably by autoclaving, for about 20 to about 40 minutes at about 122° to about 130° C. in a PAA solution. The pH of the PAA solution is preferably acidic. In a preferred embodiment, the structures are bathed in a PAA-containing solution and degassed under vacuum prior to the heat immobilization step. PAA is present in the PAA-containing solution in amounts of about 0.01 to about 3.0% wt/wt, preferably about 0.5-2.0%. The acidic conditions fall in the pH range of about pH 1.5 to about pH 5.5, usually about pH 2.85. This is a very simple and inexpensive means for anchoring PAA onto the surface of porous structures for use as an affinity agent to effectively bind LDL-C. The acidic conditions prevent the formation of undesirable side products such as calcium carbonate and silica-carbonate aggregates which can hinder the performance of the membrane. The structures formed by this process have improved binding of LDL-C in the range of 10–12 mg LDL-C per ml of fiber wall volume.

It is believed that the PAA is immobilized on the polysulfone structure by interpenetrating network (IPN). By interpenetrating network it is meant that the polyacrylic acid polymer chains intercolate into the polysulfone surface. The polysulfone surface structure relaxes during autoclaving to allow for intercolation and entanglement of the polyacrylic acid into the polysulfone surface. The final support comprises a polysulfone structure wherein polyacrylic acid is associated by interpenetrating network.

Without wishing to be bound by any theory, it is believed that the vacuum degassing step followed by the autoclaving process allows all internal surfaces to be wet by the PAA solution. This enables the PAA to be immobilized on both the outer and inner surface of the PS structure. The structure is more effective at removing LDL-C when the vacuum degassing step is performed.

During the autoclaving step, PAA can be immobilized directly to the PS structure or it can be immobilized indirectly through interactions with silica which may be embedded in the PS hollow fiber structure. Greater amounts of PAA are immobilized to the structure when silica is incorporated than without. While the actual nature of the interaction between PAA and silica is unknown, it is clear that addition of silica to the casting solution enhances the quantity of PAA bound to the structure. This step also causes the structures to be annealed and remain unaffected by subsequent autoclave steps.

A calcium ion containing molecule, such as calcium chloride can also be added in or prior to this first autoclaving step to increase again the amount of PAA immobilized to the structure, presumably by increasing the number of binding sites. The actual nature of the interaction between PAA and calcium chloride is believed to be complexation. It is clear that calcium chloride enhances the quantity of PAA bound to the structure. Calcium chloride is added to the first autoclave solution in an amount of 0.01 to 3% wt/wt, preferably about 0.4%.

E. Sterilization/Cleaning

The structure of the invention is treated in a manner to ensure that it is sterile, and also that no trace of residual solvent is present in the final structure to reduce any chance of solvent or unsterile products leaching into the patient. For sterilization/cleaning the structure is autoclaved a second time for about 20 to about 40 minutes at 120° to 130° C. in deionized water. The structure can be optionally vacuum degassed prior to this autoclave step also. The structure is washed again in water or a basic solution, such as 10 mM $NaHCO_3$ and soaked overnight in a water bath at ambient temperature containing about 5 to about 20% glycerine. It may also be desirable to have a simple salt (i.e., NaCl) and about 0.001% to about 0.1%, preferably about 0.01% of a non-ionic surfactant (i.e., TWEEN20 ® or Tween80 ®). This sterilization/cleaning process removes residual amounts of solvent and non-immobilized PAA. Unbound calcium chloride is removed by chelation. It is important that all calcium chloride is bound or removed by chelation to ensure that the structure is not hemolytic and does not cause complement activation.

It is important to note that, if the structures are autoclaved first in water, then in PAA, calcium chloride, and base, less PAA is incorporated in the structure.

F. Drying

The structure is placed in a basic solution and dried. The basic solution should be in the pH range of about 7.5 to about 10.5, preferably about Ph 8.5. In one embodiment, $NaHCO_3$ is added to the water autoclave sterilization solution. It may also be desirable to have a simple salt (i.e., NaCl) and a surfactant (i.e., TWEEN 20 ® or Tween 80 ®) in the drying solution. The salt and surfactant improve the wettability of the resulting structure. Glycerin is also added at about 5% to about 20%. The structures are placed on adsorbent paper and allowed to dry exposed to room temperature air. Alternatively, the structures can also be dried under vacuum at room temperature more quickly.

The Device

The structures are dried, preferably at room temperature in air containing less than 50% relative humidity to remove excess water. In a preferred embodiment, the structures are hollow fiber membranes. In this embodiment, the fibers are placed in a housing, and both ends of the fiber are potted in place in the housing. The preferred housing is a FOCUS®70 housing (National Medical Care, a division of W. R. Grace & Co. Connecticut) which is packed to about 42%–55% packing density with about 1200–1600 fibers per housing. Any other convenient hollow fiber housings may be used. Other similar standard device preparations are made for other structure embodiments, such as pumping plasma over a column of beads, and pumping blood or plasma through a rolled up flat sheet with spacers, etc.

Use

The polysulfone structures and the device of this invention are excellently suited for removal of LDL-C from whole blood or plasma. FIG. 1 is a schematic representation of the mechanics involved in using an LDL-C removal device of the invention wherein the polysulfone structure is a hollow fiber. Whole blood is removed from the patient, typically from a vascular access point in arm 10 using suitable blood removal apparatus 14. Some suitable apparati for blood removal include hypodermic needles, fistulas, subclavian catheters or other in-dwelling catheters. The blood passes from blood removal apparatus 14 into whole blood tubing 16 and is pumped via optional blood pump 18 into LDL-C removal device 28. As whole blood is pumped through the lumen of the hollow fiber membrane of LDL-C removal device 28, plasma is forced through the channels of the microporous fibers and separated from the cellular components of the blood. The plasma is treated in LDL-C removal device 28 exiting via plasma exit port 30. The remaining blood components (high hematocrit blood) passes down through the lumen of the membrane(s) and out exit port 34. The treated plasma is pumped via optional plasma pump 32 through plasma tubing 36 and is reunited with the high hemocrit blood at junction 44. The whole blood is then returned to the patient along with additional saline 38 added through saline tubing 40 at junction 46 as necessary via return tubing 42 to suitable blood return apparatus 12. The pressure is monitored by monitor 20 before blood enters LDL-C removal device 28, while blood is in LDL-C removal device 28 by monitor 24, and as blood exits LDL-C removal device 28 by monitor 22. Pressure can be adjusted as necessary using blood pump 18 and plasma pump 32. Alternatively, plasma only could be used in the device.

Within the LDL-C removal device the action is as follows. The nominal pore size of the hollow fiber is such that it will reject or prevent the passage of blood cells through the membrane, yet permits the free passage of plasma and specifically the high molecular weight components such as LDL-C (2–6 million Daltons) through the membrane wall structure. As the plasma passes through the wall of the membrane, it comes into direct contact with the affinity agent PAA, and LDL-C is bound to the wall surface. The plasma which exits through the outer surface of the membrane contains less LDL-C. In a single step, the hollow fiber cartridge separates the plasma from the blood, removes the LDL-C from the plasma, and returns both plasma and blood components to the patients. Under normal operating condition for treatment of whole blood (flow rate $(Q)_{Plasma} \leq 0.35 Q_{inlet}$ and transmembrane pressure (TMP) <50 mm Hg), the cartridge is saturated with LDL-C in about 20–40 minutes. The operating conditions for plasma only can include significantly higher TMP since there is no concern for blood cell hemolysis. The cartridge can be substantially regenerated with a 1.0M–0.7M salt wash with high speed flow in either direction, but optimally in the reverse direction of the blood flow. This substantial regeneration represents about 85–95% of the original binding capacity restored.

In many of the devices of the prior art, an arterial/venous fistula must be implanted in the patient prior to treatment in order to achieve blood access to support the required higher flow rates for the devices. The access is often in the form of a subclavian catheter and the implant procedure is very invasive. The implant procedure carries certain risks with it as well, such as increased chance of blood clots. The device of the present invention does not require such high flow rates, and therefore conventional direct intravenous therapy type vascular access is possible. This procedure is much less invasive and has fewer risks associated with it. The flow rates of the device of this invention are optimal when plasma outlet flow is maintained at equal to or less than 20% of the blood inlet flow rate and when the pressure difference between the blood inlet and plasma outlet (TMP) is maintained at less or equal to 40 mmHg. Back pressure is maintained on the plasma outlet flow to prevent hemolysis in accordance with standard procedures for plasmapheresis membranes.

The membranes and device of this invention dramatically reduce the amount of LDL-C from whole blood or plasma. A significant quick reduction in LDL-C levels is advantageous for some patients and cannot be obtained using drug or dietary regimens. The present device also drops LDL-C levels very selectively and effectively which is not necessarily the case for prior art devices. The invention further can facilitate plaque regression of atherosclerotic lesions insofar as reduction of circulating LDL-C levels permits.

This device is useful for reducing LDL-C in any number of increased cholesterol disorders. The primary candidates for use of the device of the invention include young individuals homozygous for familial hypercholesterolemta who have a family history of heart disease, patients with severe coronary artery disease that are non-operable, and all potential bypass candidates. The most significant and acute cholesterol disorder is hypercholesterolemia and treatment of this disorder is certainly applicable to the device of the invention.

EXAMPLES

The following examples are intended to illustrate but not to limit the invention. The following abbreviations have been used throughout in describing the invention.

dl—deciliter(s)
°C.—degrees centigrade
Q—flow rate
gm—gram(s)
HDL—high density lipoprotein
hr—hour(s)
kD—kilodalton(s)
l—liter(s)
LDL-C—low density lipoprotein cholesterol complex
m—meter(s)
ml—milliliter(s)
min—minute(s)
M—molar
%—percent
PAA—polyacrylic acid
PS—polysulfone
psi—pounds per square inch
rpm—rotations per minute
T.C.—total cholesterol
TMP—transmembrane pressure

EXAMPLE 1

Hollow Fiber Membrane Formation

A particular polysulfone structure in the form of a hollow fiber membrane is prepared as follows. Polysulfone, 210 gm (UDEL ® 1700, CAS #25135-51-7), was added to 1690 gm of 4-butyrolactone (Kodak, CAS #96-48-0), in a glass jar with a sealable top containing a teflon (or other inert) liner. The mixture was rolled continuously on a roller mill for 48–72 hours at room temperature until the polymer was dissolved. To this solution of polysulfone in 4-butyrolactone was added 100 gm of silica (SYLOX-2 ®, Davison Division of W. R. Grace & Co. Connecticut). The jar was resealed and rolled continuously on the roller mill for at least 16 hours at room temperature to disperse the silica particles. This gave a casting solution that was 10.5 wt % in Polysulfone, 5 wt % in SYLOX-2 ® and 84.5 wt % in 4-butyrolactone.

The casting solution was then centrifuged at 2,000 rpm for 10 minutes to settle any poorly suspended silica particles. Next, the casting solution was pumped through a 40 micron stainless steel screen at 60 psi of pressure with dry nitrogen gas as the source of the driving pressure. After filtration the casting solution was de-gassed under mechanical vacuum at less than 10 mmHg for at least 15 minutes and put in a stainless steel kettle that could be pressurized for delivery of casting suspensions to nozzle. No substantial solvent was lost during this degassing procedure due to the low volatility of the solvent. Under 60 psi of dry nitrogen gas, the casting solution was extruded through a glass nozzle within an orifice under the surface of a bath of deionized water. The core liquid of the spinnerette was 4-butyrolactone, driven by 80 psi dry nitrogen gas. The hollow fiber fabricated from the process during the under water spinning process was collected on a revolving wheel partially submerged under water. When the appropriate number of fibers were collected (800–1,200 revolutions), the fiber bundle was removed from the wheel, cut to chosen lengths, and soaked 16 hours at room temperature in deionized water.

EXAMPLE 2

Flat Sheet Membrane Formation

A particular polysulfone structure in the form of a flat sheet membrane is prepared as follows. Polysulfone, 210 gm (UDEL ® 1700, CAS #25135-51-7), is added to 1690 gm of 4-butyrolactone (Kodak, CAS #96-48-0), in a glass jar with a sealable top containing a teflon (or other inert) liner. The mixture is rolled continuously on a roller mill for 48–72 hours at room temperature until the polymer is dissolved. To this solution of polysulfone in 4-butyrolactone is added 100 gm of silica (SYLOX-2 ®, Davison Division of W. R. Grace & Co. Connecticut). The jar is resealed and rolled continuously on the roller mill for at least 16 hours at room temperature to disperse the silica particles. This gives a casting solution that is 10.5 wt % in Polysulfone, 5 wt % in SYLOX-2 ® and 84.5 wt % in 4-butyrolactone.

The casting solution is then centrifuged at 2,000 rpm for 10 minutes to settle any poorly suspended silica particles. Next, the casting solution is pumped through a 40 micron stainless steel screen at 60 psi of pressure with dry nitrogen gas as the source of the driving pressure. After filtration the casting solution is de-gassed under mechanical vacuum at less than 10 mmHg for at least 15 minutes and put in a stainless steel kettle that can be pressurized for delivery of casting suspensions to nozzle. No substantial solvent is lost during this degassing procedure due to the low volatility of the solvent. The casting solution is spread on a glass plate with a casting knife blade suspended 4–10 mil over the solid surface (Paul Gardner, Inc., Pompono Beach, Fla., Model No. AP-G08) and submerged in a water bath.

EXAMPLE 3

Polyacrylic Acid Immobilization

Polyacrylic acid (Case #9003-01-4) is immobilized on the polysulfone structures of Example 2 in the following process. Five (5) bundles of hollow fibers of 13-inch length, each containing 1600 fibers or a flat sheet membrane are placed in 2.5 liters of a solution of 1.0N sodium hydroxide in a stainless steel tray, de-gassed by vacuum of 28 mmHg for at least 10 minutes, and allowed to soak 16 hours at room temperature.

The structures are then rinsed with 1.25 liters of 0.5% polyacrylic acid in order to neutralize the caustic. The structures are then placed in 2.5 liters of 0.5% polyacrylic acid (pH 2.85) and 0.4% calcium chloride, degassed as above, then autoclaved for 30 minutes at 130° C. at 30 psi. The structures are then rinsed with deionized water to remove excess solution of PAA and calcium ions and autoclaved again in 2.5 liters of deionized water for 30 minutes at 130° C. at 30 psi. The structures are then removed from the autoclave solution and soaked 16 hours at room temperature in a bath containing 5% glycerin, 0.1M sodium chloride, and 0.01M sodium bicarbonate, pH=8.3.

After soaking in the glycerin bath, the structures are removed and allowed to air dry for 24 hours at room temperature on absorbent paper. The dried structures are placed in the proper size device, and both ends are potted in place with a biomedical grace epoxy-resin system (Emerson & Cummings, Division of W. R. Grace & Co. Connecticut, (Cat #674A and 674B) as per instructions. The device is now ready for testing. Once the device is tested to ensure the polysulfone structures maintained pressure as expected, it is ready to be used for removal of LDL-C from plasma and/or whole blood.

EXAMPLE 4

Device Testing

A hollow fiber device as prepared in Example 3 containing 1200 fibers with a surface area of 1356 $cm^2$ and total wall volume of 7.7 ml is perfused with plasma from a 100 ml reservoir of high cholesterol human plasma. The recirculation of high LDL-C plasma through the device is maintained at a flow rate of 58 ml/min giving a shear rate of 130 $sec^{-1}$ to achieve a steady plasma filtration rate through the walls of the fibers. Plasma samples were taken from the plasma exit port and filtrated at time 0, 30 minutes, and 60 minutes. The average transmembrane pressure (TMP) remained constant throughout the run at 100 mmHg. Plasma filtrate flux values were 5.3 $1/hr/m^2$ at 30 minutes and 4.9 $1/hr/m^2$ at 60 minutes. Total cholesterol assays were performed on the plasma reservoirs using the Kodak EKTACHEM® DT60 and nephelometry (Beckman Auto ICS Catalog Number 449310) to determine the level of the LDL-C associated protein apolipoprotein B.

The total cholesterol (T.C.) level is reduced from an initial value of 289 mg/dl to 175 mg/dl. The apolipoprotein B concentration is reduced form 173 mg/dl to 78 mg/dl. The total protein levels, also determined on the Kodak EKTACHEM® DT60, went from 7.8 mg/dl to 7.0 mg/dl. The difference in the pre- and post-total cholesterol values is used to determine the amount of T.C. removed from the plasma reservoir and a drop of 39.4% is observed. This corresponds to a binding of 14.8 mg total cholesterol per ml. of fiber wall volume.

EXAMPLE 5

Device Testing

A flat sheet membrane as prepared in Example 3 containing a 5 inch×2.75 inch flat sheet having a total wall volume of 0.7886 ml. The membrane is rolled up and placed in a test tube containing 15 ml high cholesterol human plasma. The tube is shaken twice and allowed to sit undisturbed overnight for 21 hours. Total cholesterol assays are performed on the plasma reservoirs using the Kodak EKTACHEM® DT60.

The total cholesterol (T.C.) level is reduced from an initial value of 238 mg/dl to 217 mg/dl. A similar membrane which had not been treated with PAA showed negligible T.C. reduction (238 to 136 mg/dl). The total protein levels, also determined on the Kodak EKTACHEM® DT60, went from 4.9 mg/dl to 5.1 mg/dl for both membranes. The difference in the pre- and post-total cholesterol values is used to determine the amount of T.C. removed from the plasma reservoir and a loss of 3.15 mg of T.C. from bulk solution is observed. This corresponds to a binding of 4 mg total cholesterol per ml. of membrane wall volume.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A support for binding low density lipoprotein cholesterol comprising a microporous polysulfone structure having pore diameters in the range from about 0.1 microns to about 0.7 microns and having an amount of polyacrylic acid effective to bind low density lipoprotein cholesterol immobilized by an interpenetrating network on the surface of said polysulfone structure.

2. The support of claim 1 wherein said structure is a flat sheet membrane.

3. The support of claim 1 wherein said structure is a bead.

4. A support for binding low density lipoprotein cholesterol comprising a microporous polysulfone structure having pore diameters in the range of from about 0.1 microns to about 0.7 microns and having polyacrylic acid and a calcium ion containing compound immobilized by an interpenetrating network on the surface of said polysulfone structure, wherein the amount of polyacrylic acid is effective to bind low density lipoprotein cholesterol and the calcium ion containing compound is in an amount effective to enhance the quantity of polyacrylic acid immobilized on the structure.

5. A support for binding low density lipoprotein cholesterol comprising a microporous polysulfone structure having pore diameters in the range of from about 0.1 microns to about 0.7 microns and having polyacrylic acid, a calcium ion containing compound and silica immobilized by an interpenetrating network on the surface of said polysulfone structure, wherein the amount of polyacrylic acid is effective to bind low density lipoprotein cholesterol and the calcium ion containing compound and silica are in an amount effective to enhance the quantity of polyacrylic acid immobilized on the structure.

6. The support of claim 1, wherein said pore diameter ranges from about 0.4 microns to about 0.65 microns.

7. The support of claim 4, wherein said pore diameter ranges from about 0.4 microns to about 0.65 microns.

8. The support of claim 5, wherein said pore diameter ranges from about 0.4 microns to about 0.65 microns.

* * * * *